(12) United States Patent
Pujol et al.

(10) Patent No.: US 10,617,776 B2
(45) Date of Patent: Apr. 14, 2020

(54) GAS DELIVERY SYSTEM AND METHOD OF SANITIZING THE GAS FLOW PATH WITHIN A GAS DELIVERY SYSTEM

(71) Applicant: KONINKLIJKE PHILIPS N.V., Eindhoven (NL)

(72) Inventors: John Raymond Pujol, Murrysville, PA (US); David Scott Arnold, North Huntingdon, PA (US); John Michael Cosnek, Pittsburgh, PA (US); Christopher Randall Baker, N Huntingdon, PA (US); Mark William Dimatteo, Irwin, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/168,188

(22) Filed: Oct. 23, 2018

(65) Prior Publication Data
US 2019/0054199 A1    Feb. 21, 2019

Related U.S. Application Data

(62) Division of application No. 15/105,623, filed as application No. PCT/IB2014/066994 on Dec. 17, 2014, now Pat. No. 10,130,726.
(Continued)

(51) Int. Cl.
*A61L 2/10* (2006.01)
*A61M 16/00* (2006.01)
(Continued)

(52) U.S. Cl.
CPC .................... *A61L 2/10* (2013.01); *A61L 9/20* (2013.01); *A61M 16/0066* (2013.01); *A61M 16/04* (2013.01); *A61M 16/0666* (2013.01); *A61M 16/0875* (2013.01); *A61M 16/16* (2013.01); *A61M 16/201* (2014.02); *A61L 2202/11* (2013.01); *A61L 2202/24* (2013.01); *A61L 2209/16* (2013.01); *A61M 2016/003* (2013.01);
(Continued)

(58) Field of Classification Search
CPC .......................... A61L 2/10; A61M 16/0066
See application file for complete search history.

(56) References Cited

U.S. PATENT DOCUMENTS

| 5,148,802 A | 9/1992 | Sanders et al. |
| 5,313,937 A | 5/1994 | Zdrojkowski |

(Continued)

FOREIGN PATENT DOCUMENTS

| CN | 2785652 Y | 6/2006 |
| CN | 202376593 U | 8/2012 |

(Continued)

*Primary Examiner* — Kevin Joyner

(57) ABSTRACT

A gas delivery system (50) for delivering a flow of breathing gas to a patient (54) includes a blower assembly (100) structured to generate the flow of breathing gas. The blower assembly includes a gas flow path including an inlet manifold, an assembly (130) structured to adjust a pressure and/or flow rate of the flow of breathing gas, and an outlet manifold structured to be coupled to a patient circuit. The gas delivery system additionally includes a light system structured to generate sanitizing light and deliver the sanitizing light to one or more internal surfaces of at least one of the inlet manifold, the assembly and the outlet manifold for sanitizing the one or more internal surfaces.

20 Claims, 15 Drawing Sheets

Related U.S. Application Data

(60) Provisional application No. 61/917,394, filed on Dec. 18, 2013.

(51) Int. Cl.

| | | |
|---|---|---|
| *A61L 9/20* | (2006.01) | |
| *A61M 16/20* | (2006.01) | |
| *A61M 16/04* | (2006.01) | |
| *A61M 16/06* | (2006.01) | |
| *A61M 16/08* | (2006.01) | |
| *A61M 16/16* | (2006.01) | |
| *A61M 39/16* | (2006.01) | |

(52) U.S. Cl.
CPC ... *A61M 2039/167* (2013.01); *A61M 2209/10* (2013.01)

(56) References Cited

U.S. PATENT DOCUMENTS

| | | | |
|---|---|---|---|
| 5,433,193 A | 7/1995 | Sanders et al. | |
| 5,632,269 A | 5/1997 | Zdrojkowski | |
| 5,803,065 A | 9/1998 | Zdrojkowski et al. | |
| 5,855,203 A | 1/1999 | Matter | |
| 6,029,664 A | 2/2000 | Zdrojkowski et al. | |
| 6,443,147 B1 | 9/2002 | Matter | |
| 6,470,888 B1 | 10/2002 | Matter | |
| 6,539,940 B2 | 4/2003 | Zdrojkowski et al. | |
| 6,626,175 B2 | 9/2003 | Jafari et al. | |
| 6,983,745 B2 | 1/2006 | Tang et al. | |
| 7,011,091 B2 | 3/2006 | Hill et al. | |
| 2007/0102280 A1 | 5/2007 | Hunter et al. | |
| 2007/0163588 A1 | 7/2007 | Hebrank et al. | |
| 2007/0169776 A1 | 7/2007 | Kepler et al. | |
| 2009/0004047 A1 | 1/2009 | Hunter et al. | |
| 2009/0126731 A1 | 5/2009 | Dunsmore et al. | |
| 2009/0173344 A1 | 7/2009 | Short | |
| 2010/0175694 A1 | 7/2010 | James et al. | |
| 2013/0028710 A1 | 1/2013 | Kenyon et al. | |
| 2014/0030144 A1 | 1/2014 | Krosney | |
| 2014/0060537 A1 | 3/2014 | Hansmann et al. | |

FOREIGN PATENT DOCUMENTS

| | | |
|---|---|---|
| CN | 202822393 U | 3/2013 |
| DE | 102012003549 A1 | 8/2013 |
| DE | 102012221839 B3 | 8/2013 |
| GB | 1488018 A | 10/1977 |
| WO | 02065972 A2 | 8/2002 |

GAS DELIVERY SYSTEM AND METHOD OF SANITIZING THE GAS FLOW PATH WITHIN A GAS DELIVERY SYSTEM

CROSS-REFERENCE TO PRIOR APPLICATIONS

This application is a divisional application of U.S. National Phase application under 35 U.S.C. § 371, Ser. No. 15/105,623, filed on Jun. 17, 2016, which claims the benefit of International Application Ser. No. PCT/IB2014/066994, filed on Dec. 17, 2014, which claims the benefit of U.S. application Ser. No. 61/917,394, filed on Dec. 18, 2013. These applications are hereby incorporated by reference herein.

BACKGROUND OF THE INVENTION

1. Field of the Invention

The present invention relates to gas delivery systems, such as, without limitation, PAP therapy systems for treating sleep apnea, ventilators, oxygen delivery systems, or other respiratory devices, and more particularly to methods of sanitizing the gas flow path within such gas delivery systems.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypoapnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypoapneas of the patient.

It is well known to treat sleep disordered breathing by applying a positive air pressure (PAP) to the patient's airway. This positive pressure effectively "splints" the airway, thereby maintaining an open passage to the lungs. In one type of PAP therapy, known as continuous positive air pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

In known gas delivery systems, an unclean gas flow path can lead to organisms, such as bacteria, viruses, fungi, or mold, being inhaled by the patient. These organisms, which usually grow in warm and moist locations, can cause harm to the patient. This often occurs when the same gas delivery system is used by multiple patients, such as in the PAP therapy system rental market, where the risk for the spread of disease is increased. One known method is to use a bacterial filter at the outlet of the device to prevent the backflow of bacteria from a patient into the PAP device. Another known method which addresses this problem involves using steam autoclaves or other gas sterilization devices to sterilize the gas flow path of a gas delivery system. However, the use of such devices is not cost efficient, and can also damage sensitive components within the gas delivery system. A further known method of sterilizing the gas flow path of a gas delivery system involves using cleaning agents, such as a cold sterilant, vinegar, alcohol, or soap and water, to clean the gas delivery system. However, such agents can likewise damage sensitive components of gas delivery systems and can also leave harmful residue that can be inhaled by the patient.

Furthermore, the problems just described are not limited to gas delivery systems in the form of PAP therapy systems for treating sleep apnea. Rather, such problems exist in connection with any type of gas delivery system used to deliver a flow of breathing gas to a patient, such as, without limitation, ventilators, oxygen delivery systems, or other respiratory devices.

There is thus room for improvement in field gas delivery systems, and in particular to the methods used to sterilize such gas delivery systems.

SUMMARY OF THE INVENTION

In one embodiment, a gas delivery system is provided for delivering a flow of breathing gas to a patient. The gas delivery system includes a blower assembly structured to generate the flow of breathing gas. The blower assembly includes a gas flow path including an inlet manifold, an assembly, such as an impeller assembly, for adjusting the pressure and/or flow rate of the breathing gas, and an outlet manifold structured to be coupled to a patient circuit. The gas delivery system additionally includes a light system structured to generate sanitizing light and deliver the sanitizing light to one or more internal surfaces of at least one of the inlet manifold, the impeller assembly and the outlet manifold for sanitizing the one or more internal surfaces.

In another embodiment, a method of sanitizing a gas flow path within a gas delivery system including a blower assembly is provided. The gas flow path includes an inlet manifold, an assembly, such as an impeller assembly, for adjusting the pressure and/or flow rate of the breathing gas, and an outlet manifold structured to be coupled to a patient circuit. The blower assembly is structured to generate a flow of breathing gas and includes the gas flow path. The method includes the steps of: providing a light system as part of the gas delivery system, generating sanitizing light using the light system, and delivering the sanitizing light to one or more internal surfaces of at least one of the inlet manifold, the impeller assembly, and the outlet manifold for sanitizing the one or more internal surfaces.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
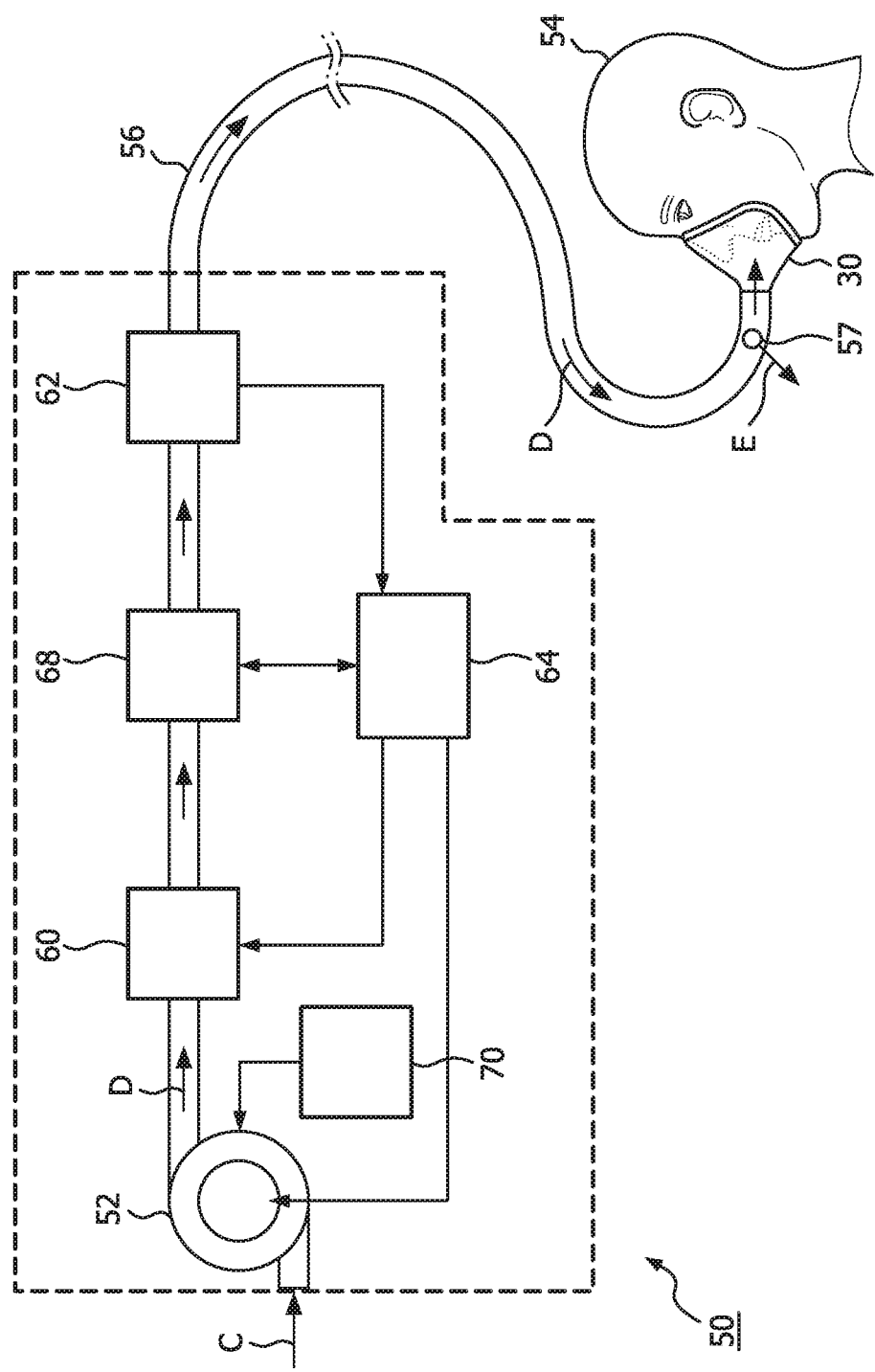
FIG. 1 is a schematic diagram of a pressure support system according to one particular, non-limiting embodiment in which the present invention in its various embodiments may be implemented.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the term "number" shall mean one or an integer greater than one (i.e., a plurality).

As employed herein, the term "manifold" shall mean a member having one or more tubes or chambers through which a liquid or gas may be distributed.

FIG. 1 is a schematic diagram of a pressure support system 50 according to one particular, non-limiting embodiment in which the present invention in its various embodiments may be implemented. Referring to FIG. 1, pressure support system 50 includes a gas flow generator 52, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of a patient 54 at relatively higher and lower pressures, i.e., generally equal to or above ambient atmospheric pressure.

In an exemplary embodiment, gas flow generator 52 is capable of providing a flow of breathing gas ranging in pressure from 3-30 cm $H_2O$. The pressurized flow of breathing gas, generally indicated by arrow D from gas flow generator 52, is delivered via a delivery conduit 56 to a breathing mask or patient interface 58 of any known construction, which is typically worn by or otherwise attached to patient 54 to communicate the flow of breathing gas to the airway of patient 54. Delivery conduit 56 and patient interface device 58 are typically collectively referred to as a patient circuit.

Pressure support system 50 shown in FIG. 1 is what is known as a single-limb system, meaning that the patient circuit includes only delivery conduit 56 connecting patient 54 to pressure support system 50. As such, an exhaust vent 57 is provided in delivery conduit 56 for venting exhaled gasses from the system as indicated by arrow E. It should be noted that exhaust vent 57 can be provided at other locations in addition to or instead of in delivery conduit 56, such as in patient interface device 58. It should also be understood that exhaust vent 57 can have a wide variety of configurations depending on the desired manner in which gas is to be vented from pressure support system 50.

The present invention also contemplates that pressure support system 50 can be a two-limb system, having a delivery conduit and an exhaust conduit connected to patient 54. In a two-limb system (also referred to as a dual-limb system), the exhaust conduit carries exhaust gas from patient 54 and includes an exhaust valve at the end distal from patient 54. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 58 is a nasal/oral mask. It is to be understood, however, that patient interface 58 can include a nasal mask, nasal pillows, a tracheal tube, an endotracheal tube, or any other device that provides a suitable gas flow communicating function. Also, for purposes of the present invention, the phrase "patient interface" can include delivery conduit 56 and any other structures that connect the source of pressurized breathing gas to patient 54.

In the illustrated embodiment, pressure support system 50 includes a pressure controller in the form of a valve 60 provided in delivery conduit 56. Valve 60 controls the pressure of the flow of breathing gas from flow generator 52 that is delivered to patient 54. For present purposes, flow generator 52 and valve 60 are collectively referred to as a pressure generating system because they act in concert to control the pressure and/or flow of gas delivered to patient 54. However, it should be apparent that other techniques for controlling the pressure of the gas delivered to patient 54, such as varying the blower speed of flow generator 52, either alone or in combination with a pressure control valve, are contemplated by the present invention. Thus, valve 60 is optional depending on the technique used to control the pressure of the flow of breathing gas delivered to patient 54. If valve 60 is eliminated, the pressure generating system corresponds to flow generator 52 alone, and the pressure of gas in the patient circuit is controlled, for example, by controlling the motor speed of flow generator 52.

Pressure support system 50 further includes a flow sensor 62 that measures the flow of the breathing gas within delivery conduit 56. In the particular embodiment shown in FIG. 1, flow sensor 62 is interposed in line with delivery conduit 56, most preferably downstream of valve 60. Flow sensor 62 generates a flow signal, $Q_{measured}$, that is provided to a controller 64 and is used by controller 64 to determine the flow of gas at patient 54 ($Q_{patient}$).

Techniques for calculating $Q_{patient}$ based on $Q_{measured}$ are well known, and take into consideration the pressure drop of the patient circuit, known leaks from the system, i.e., the intentional exhausting of gas from the circuit as indicated by arrow E in FIG. 1, and unknown leaks from the system, such as leaks at the mask/patient interface. The present invention contemplates using any known or hereafter developed technique for calculating leak flow $Q_{leak}$, and using this determination in calculating $Q_{patient}$ based on $Q_{measured}$. Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 54 are contemplated by the present invention, such as, without limitation, measuring the flow directly at patient 54 or at other locations along delivery conduit 56, measuring patient flow based on the operation of flow generator 52, and measuring patient flow using a flow sensor upstream of valve 60.

Controller 64 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 50, including controlling the emission of ultraviolet light as described in greater detail herein.

In the illustrated embodiment, pressure support system 50 also includes humidifier 68 provided in the main housing of pressure support system 50. Alternatively, humidifier 68 may be separate from and located external to the main housing. Humidifier 68 is controlled by controller 64. Humidifier 68 further improves comfort by providing moisture in the supplied gas. In the exemplary embodiment, humidifier 68 is a passover type humidifier. U.S. Patent Application Publication No. 2007/0169776, incorporated herein by reference in its entirety, discloses an exemplary humidifier device suitable for use in the present invention. Humidifier devices having alternative designs, such as a non-passover type humidifier that employs nebulization, atomization, vaporization or a combination thereof, may also be used.

In the illustrated, non-limiting embodiment of the present invention, pressure support system 50 essentially functions as a CPAP pressure support system, and, therefore, includes all of the capabilities necessary in such systems in order to provide appropriate CPAP pressure levels to patient 54. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Figure 2:
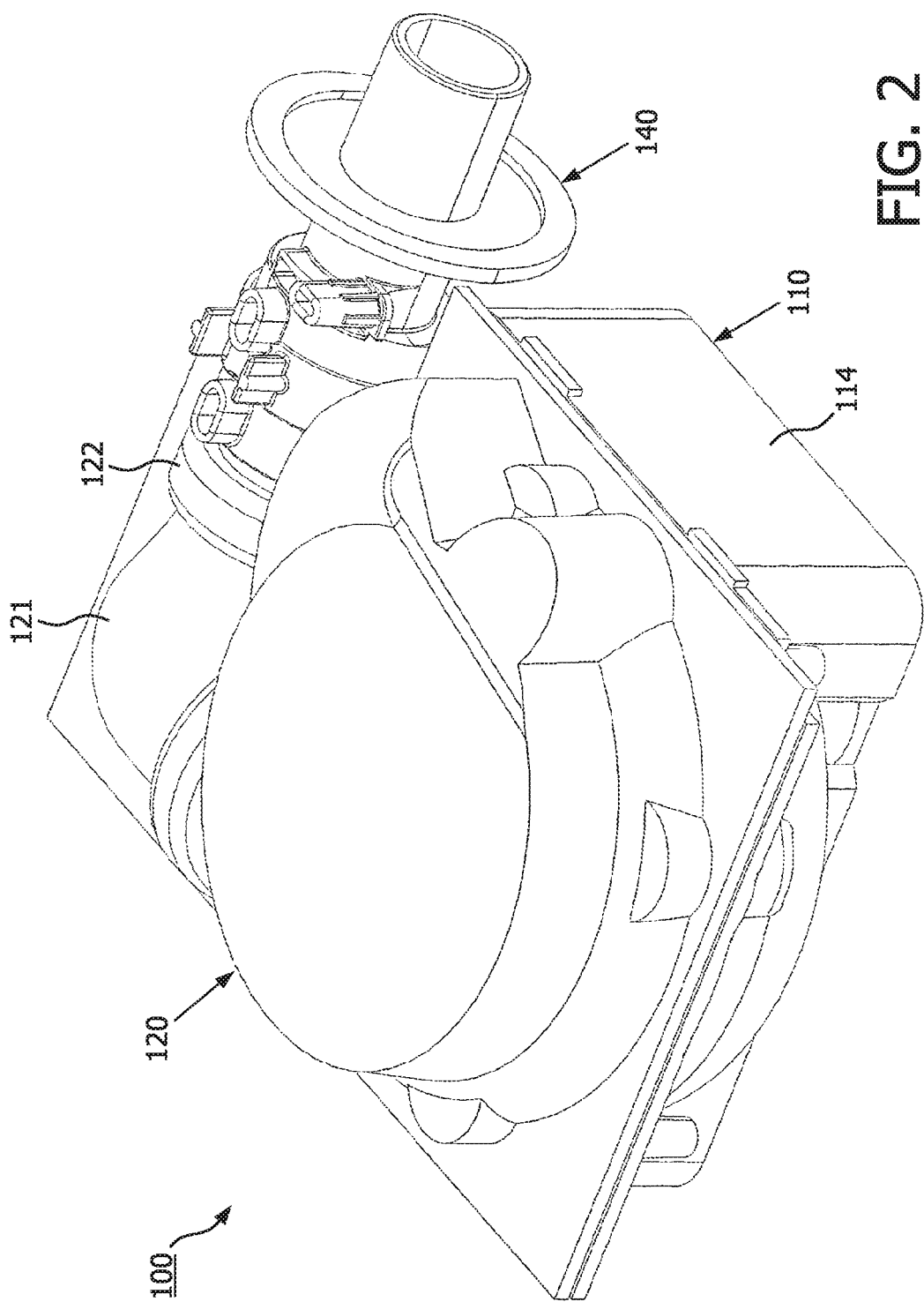
FIG. 2 is a top isometric view of a blower assembly in accordance with the disclosed concept.
Figure 3:
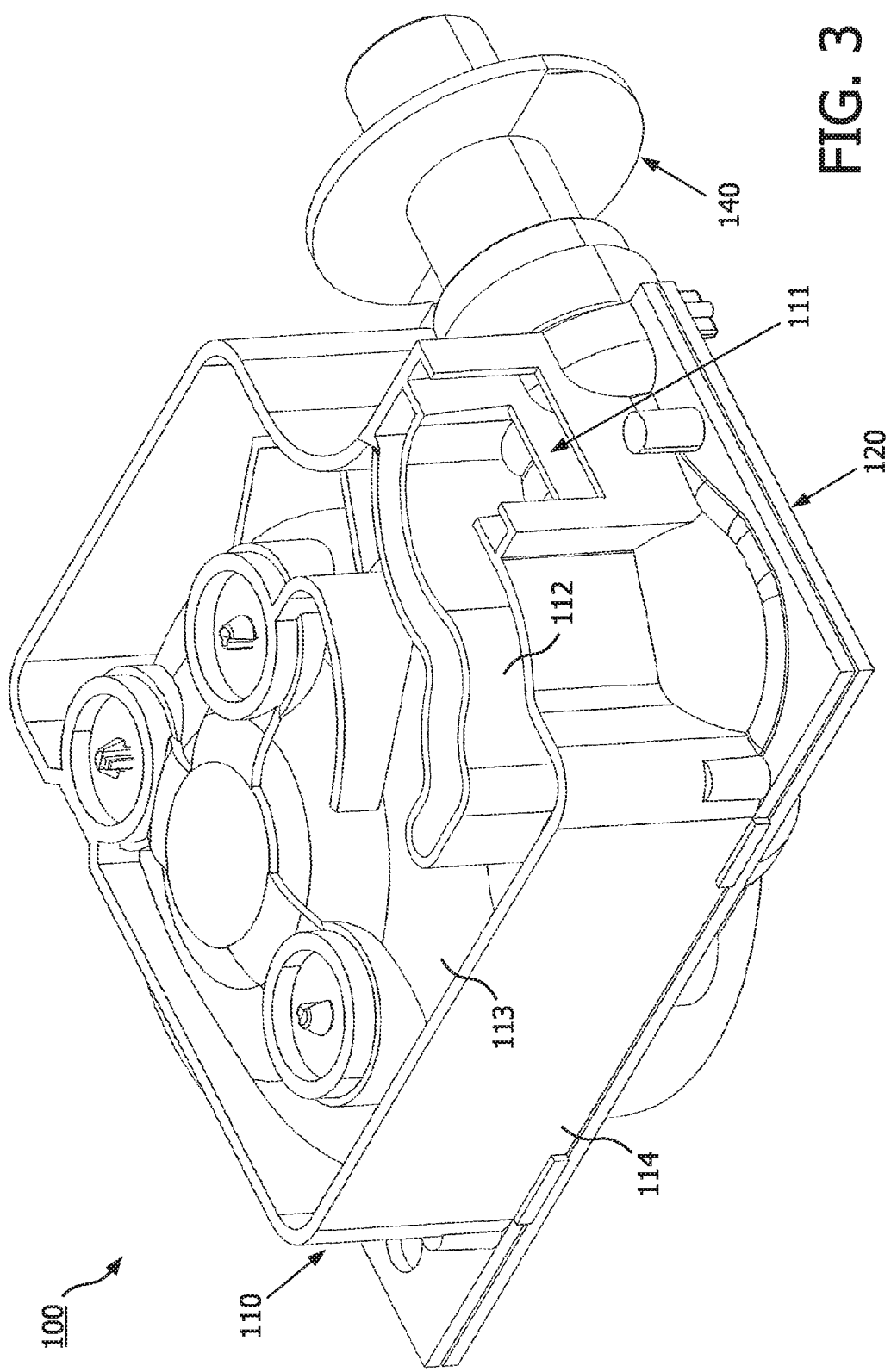
FIG. 3 is a bottom isometric view of the blower assembly of FIG. 2.
Figure 4:
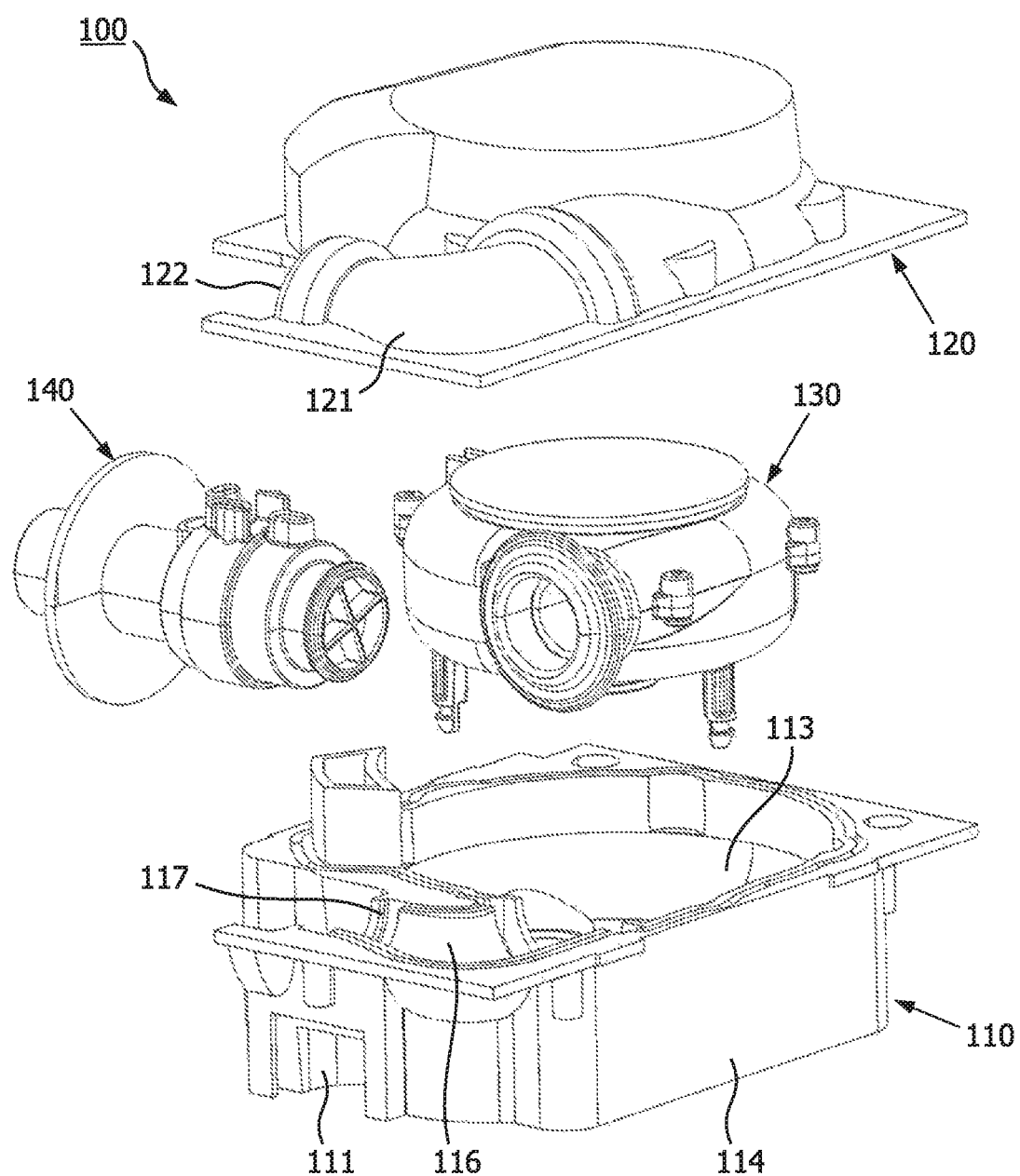
FIG. 4 is an exploded isometric view of the blower assembly of FIG. 2.
Figure 5:
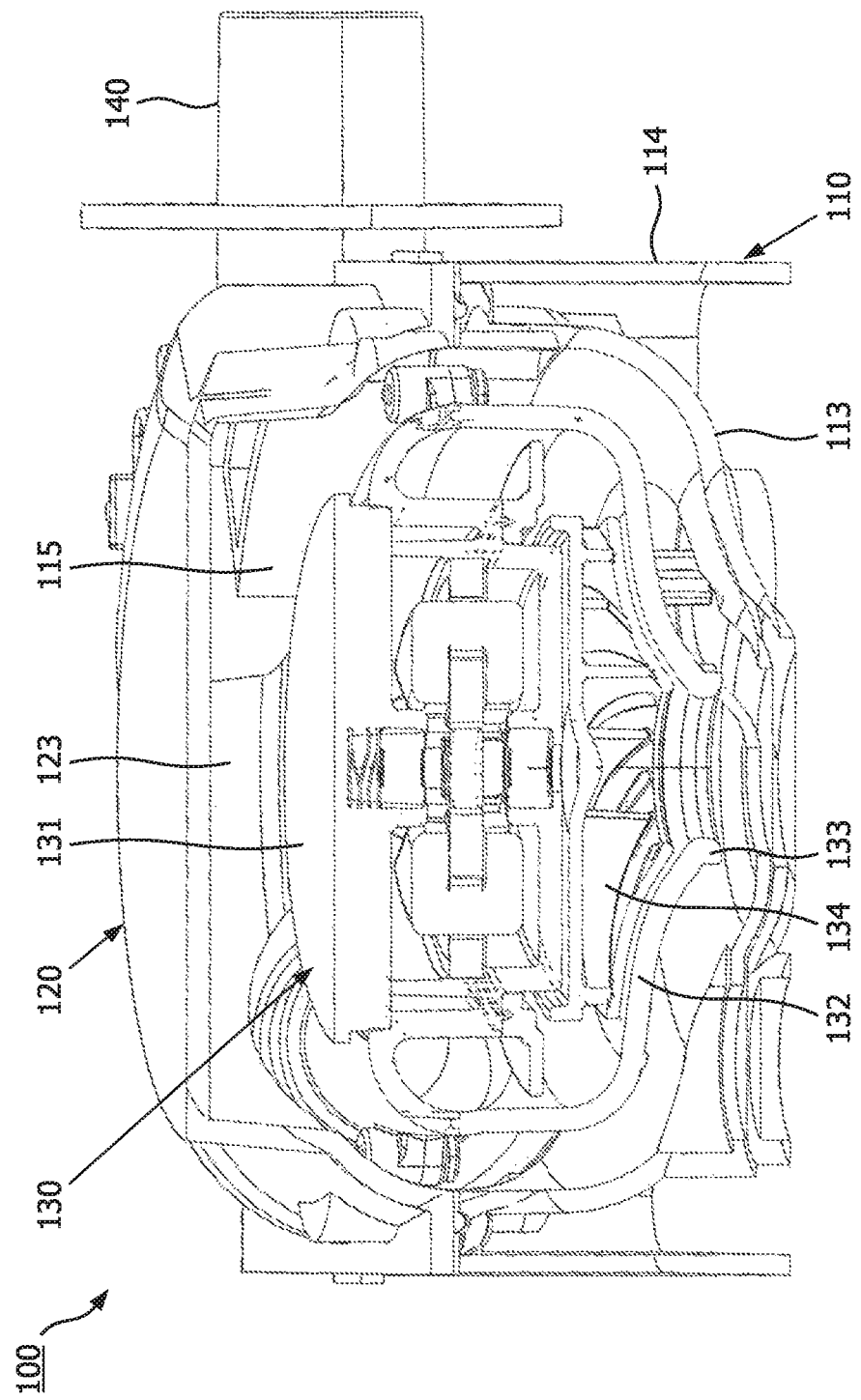
FIG. 5 is a cross-sectional view of the blower assembly of FIG. 2.

FIG. 2 is a top isometric view, FIG. 3 is a bottom isometric view, FIG. 4 is an exploded isometric view, and FIG. 5 is a cross-sectional view of a blower assembly 100 that may be used in pressure support system 50 to implement flow generator 52 according to an exemplary embodiment. As seen in FIGS. 2-5, blower assembly 100 includes a lower housing 110, an upper housing 120, an impeller assembly 130 located between and housed between lower housing 110 and upper housing 120, and an outlet conduit 140. Impeller assembly 130, described in more detail below, is structured to take in gas introduced through lower housing 110 and expel that gas at an altered (e.g., a higher) pressure and/or flow rate through outlet conduit 140, which in turn is coupled to the patient circuit.

Figure 6:
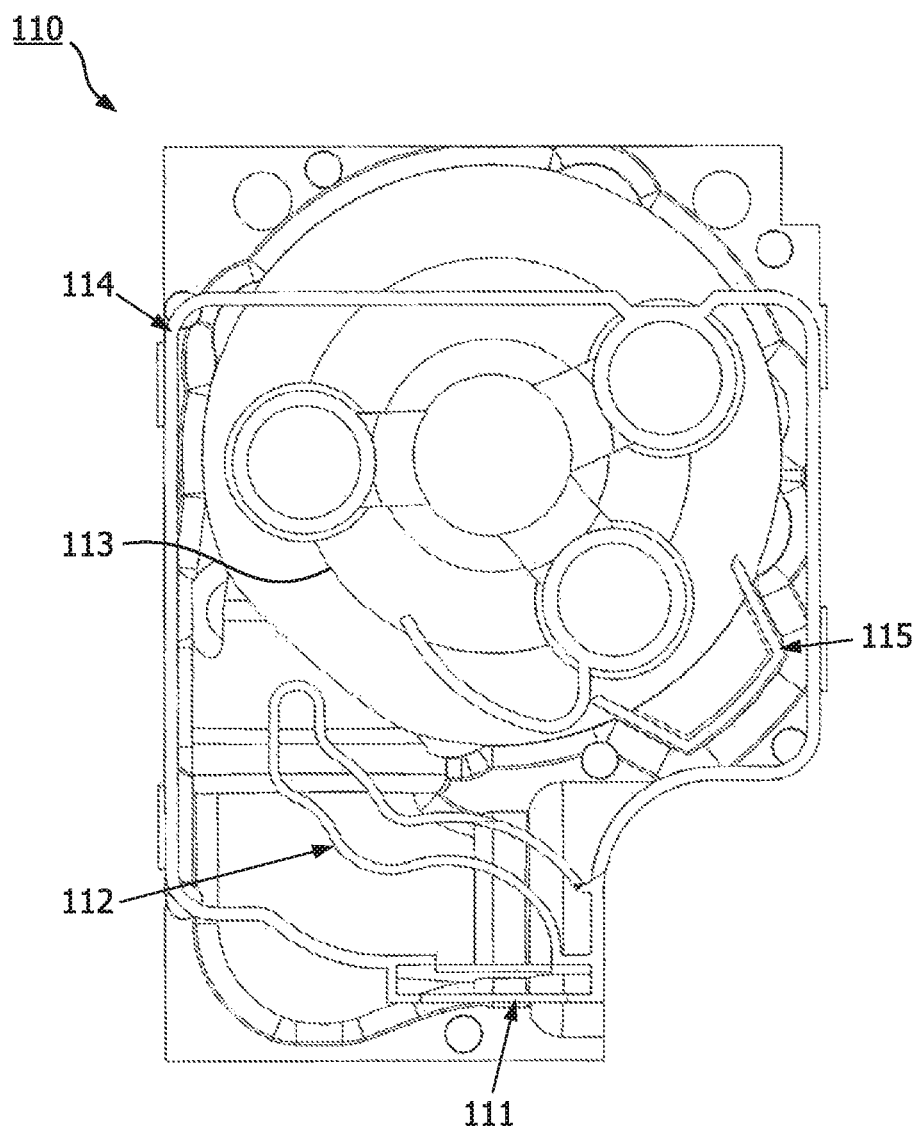
FIG. 6 is a bottom plan view of a lower housing of the blower assembly of FIG. 2.
Figure 7:
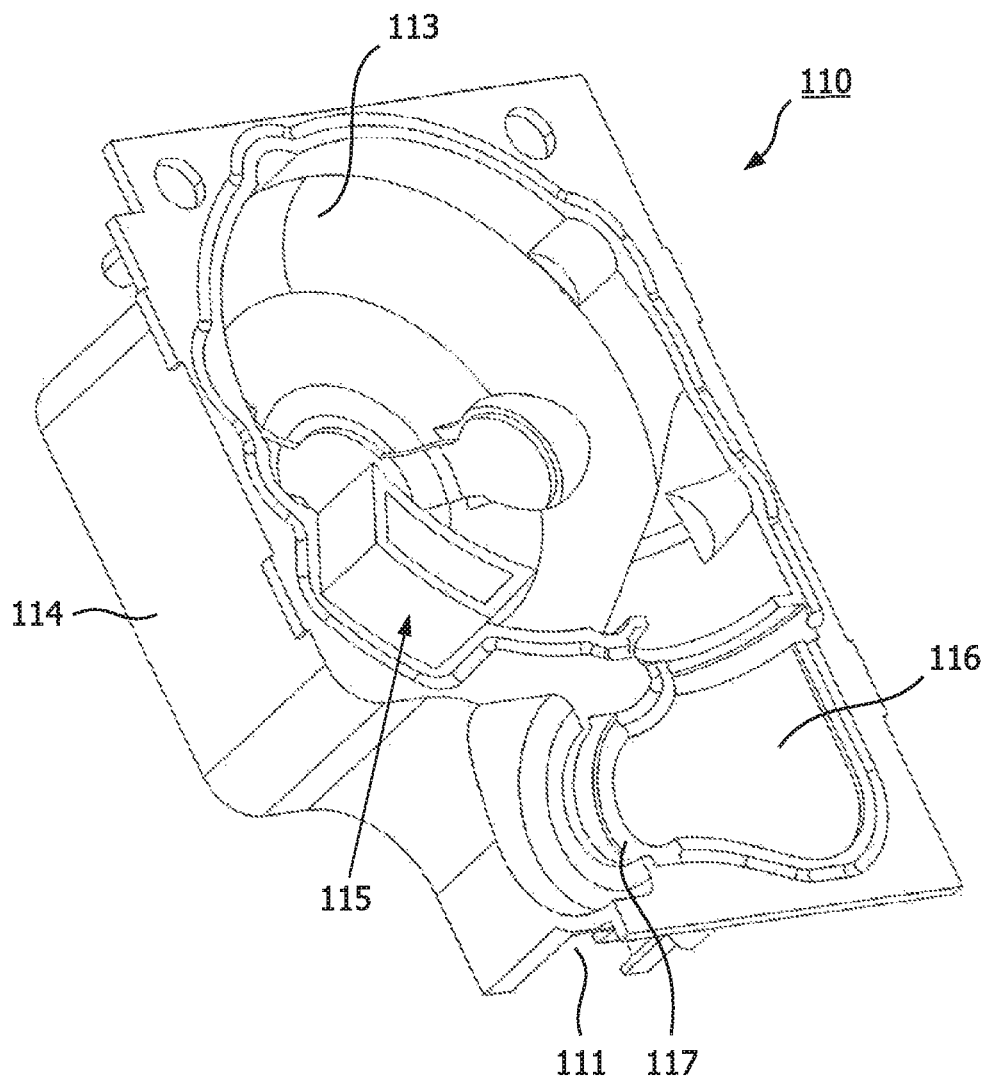
FIG. 7 is a top isometric view of the lower housing of FIG. 6.

Referring to FIG. 6, which is a bottom plan view of lower housing 110, and FIG. 7, which is a top isometric view of lower housing 110, lower housing 110 includes an inlet opening 111 through which gas enters, a directing wall 112, and a body portion 113. After gas enters, it flows past directing wall 112 and over body portion 113. As shown, lower housing 110 further includes a containment wall 114 located along an outer periphery of lower housing 110 and a port 115. Containment wall 114 is structured to be sealingly engaged to a bottom plate or housing member (not shown) of pressure support system 50 such that when gas is pulled over body portion 113, it is contained and forced through port 115. As seen in FIG.7, lower housing 110 also includes a partial conduit 116 and a coupling portion 117, the functions of which are described elsewhere herein.

Figure 8:
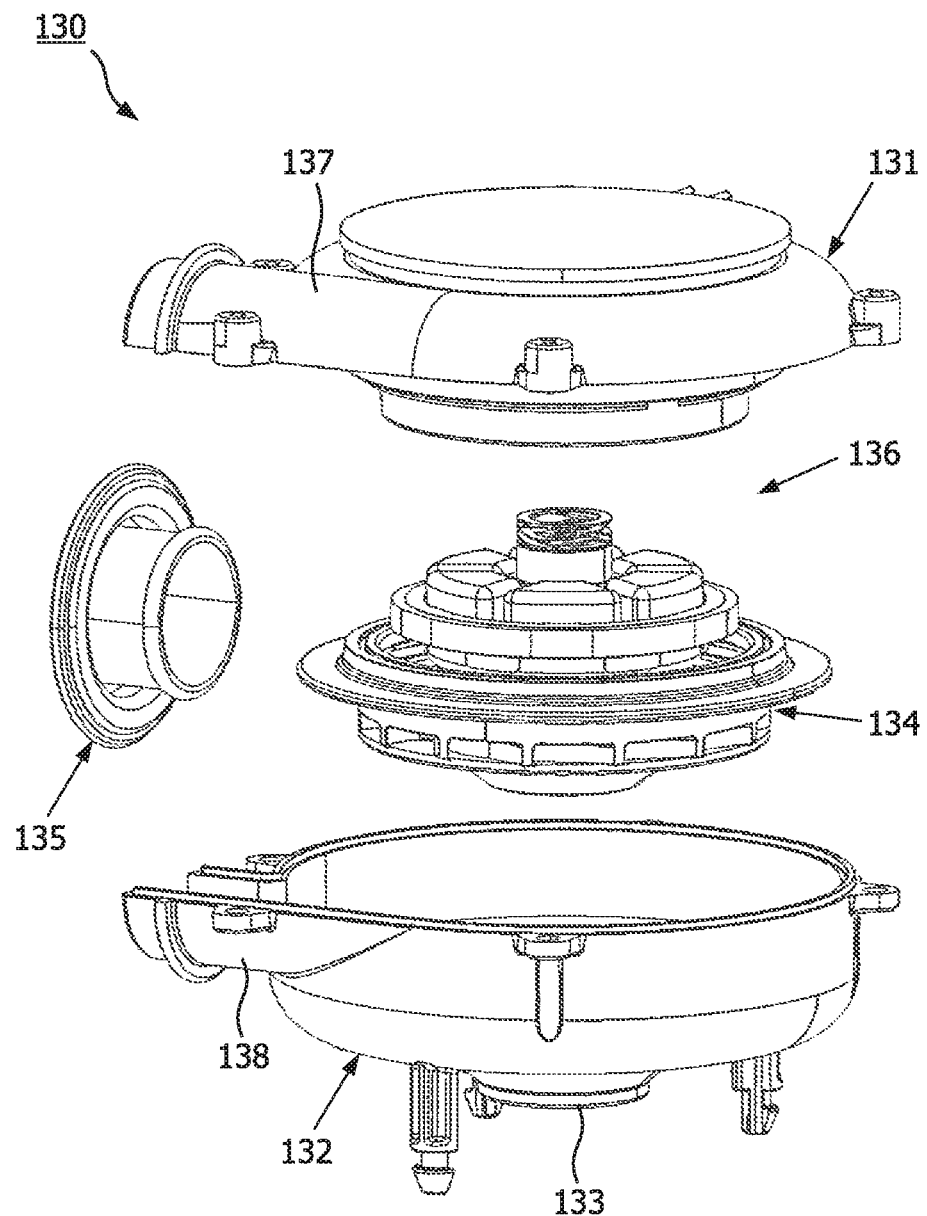
FIG. 8 is an exploded isometric view of an impeller assembly of the blower assembly of FIG. 2.

Referring to FIG. 5 and to FIG. 8, which is an exploded view of impeller assembly 130, impeller assembly 130 includes an upper housing 131, a lower housing 132 having an inlet port 133, and an impeller 134 held in between upper housing 131 and lower housing 132. Impeller assembly 130 also includes an outlet member 135 structured to be held in between a partial conduit portion 137 of upper housing 131 and a partial conduit portion 138 of lower housing 132 to thereby form an outlet conduit for impeller assembly 130. Alternatively, impeller assembly 130 may be replaced by an assembly that includes a compressor, a fan, a blower, a piston or a bellows.

Figure 9:
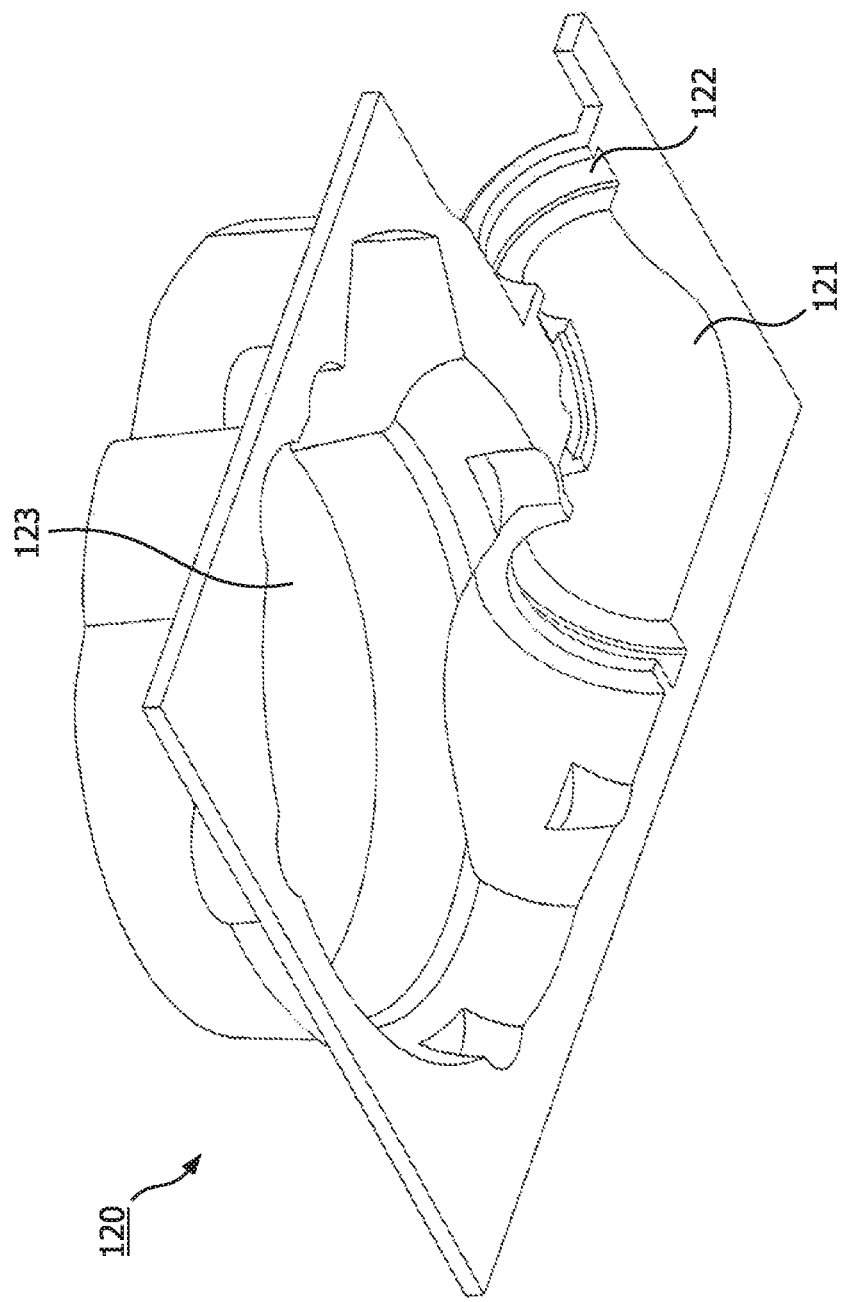
FIG. 9 is a bottom isometric view of an upper housing of the blower assembly of FIG. 2.

FIG. 9 is a bottom isometric view of upper housing 120. As seen, upper housing 120 includes a partial conduit 121, a coupling portion 122, and a chamber 123. Lower housing 110 and upper housing 120 are structured such that, when coupled to each other, partial conduits 116,121 are aligned and coupling portions 117,122 are aligned. Furthermore, and with reference to FIG. 4, outlet conduit 140 is structured to be located and held in between coupling portions 117,122.

In operation, breathing gas, such as, without limitation, air or oxygen, enters lower housing 110 through inlet opening 111. The gas is then directed by directing wall 112 to the area defined by the bottom of body portion 113 and containment wall 114. From there, the gas flows through port 115 to the area defined by chamber 123 of upper housing 120. The gas then flows down over the exterior of impeller assembly 130 to the top of body portion 113 where it is directed into inlet port 133 of impeller assembly 130. Inside impeller assembly 130, the pressure and/or flow rate of the gas is increased by operation of impeller 134. The gas is then expelled from impeller assembly 130 through the outlet conduit formed by outlet member 135, partial conduit portion 137 and partial conduit portion 138. The expelled gas is received in the conduit member formed by partial conduits 116,121, coupling portions 117,122 and outlet conduit 140, and thereafter delivered to the patient through the patient circuit as described herein.

Thus, as just described, blower assembly 100 has three main portions: (i) an "inlet manifold" for delivering breathing gas to impeller assembly 130 that includes inlet opening 111, directing wall 112, body portion 113, containment wall 114, port 115 and chamber 123, (ii) impeller assembly 130 for adjusting the pressure and/or flow rate of the breathing gas, and (iii) an "outlet manifold" for delivering the breathing gas to the patient circuit that includes partial conduits 116,121, coupling portions 117,122 and outlet conduit 140.

Furthermore, as seen in FIG. 1 and in accordance with the disclosed concept, pressure support system 50 is also provided with an ultraviolet light system 70 that, in the exemplary embodiment, is structured to generate $UV_c$ ultraviolet light to sanitize the gas flow path (including the inlet manifold, the impeller assembly 130 and the outlet manifold as just described) within flow generator 52. More specifically, when $UV_c$ ultraviolet light is caused to contacts the surfaces within flow generator 52, namely the surfaces of the inlet manifold, impeller assembly 130, and the outlet manifold, it will kill organisms living on those surfaces by altering the DNA of such organisms, advantageously preventing them from reproducing and thereby resulting in a safer and healthier air path for a user. In the non-limiting exemplary embodiment, ultraviolet light system 70 emits $UV_c$ ultraviolet light in the range of 100 to 400 nanometers. In one specific embodiment, $UV_c$ light is emitted in the range of 200 to 280 nanometers.

As will be appreciated, blower assembly 100 and ultraviolet light system 70 may be implemented in a number of different ways in order to provide a safer and healthier air path for a user of pressure support system 50. A number of non-limiting, alternative exemplary implementations of blower assembly 100 and ultraviolet light system 70 are described below in connection with FIGS. 10-15. Each such implementation may be used in pressure support system 50 to sanitize the gas flow path thereof.

Figure 10:
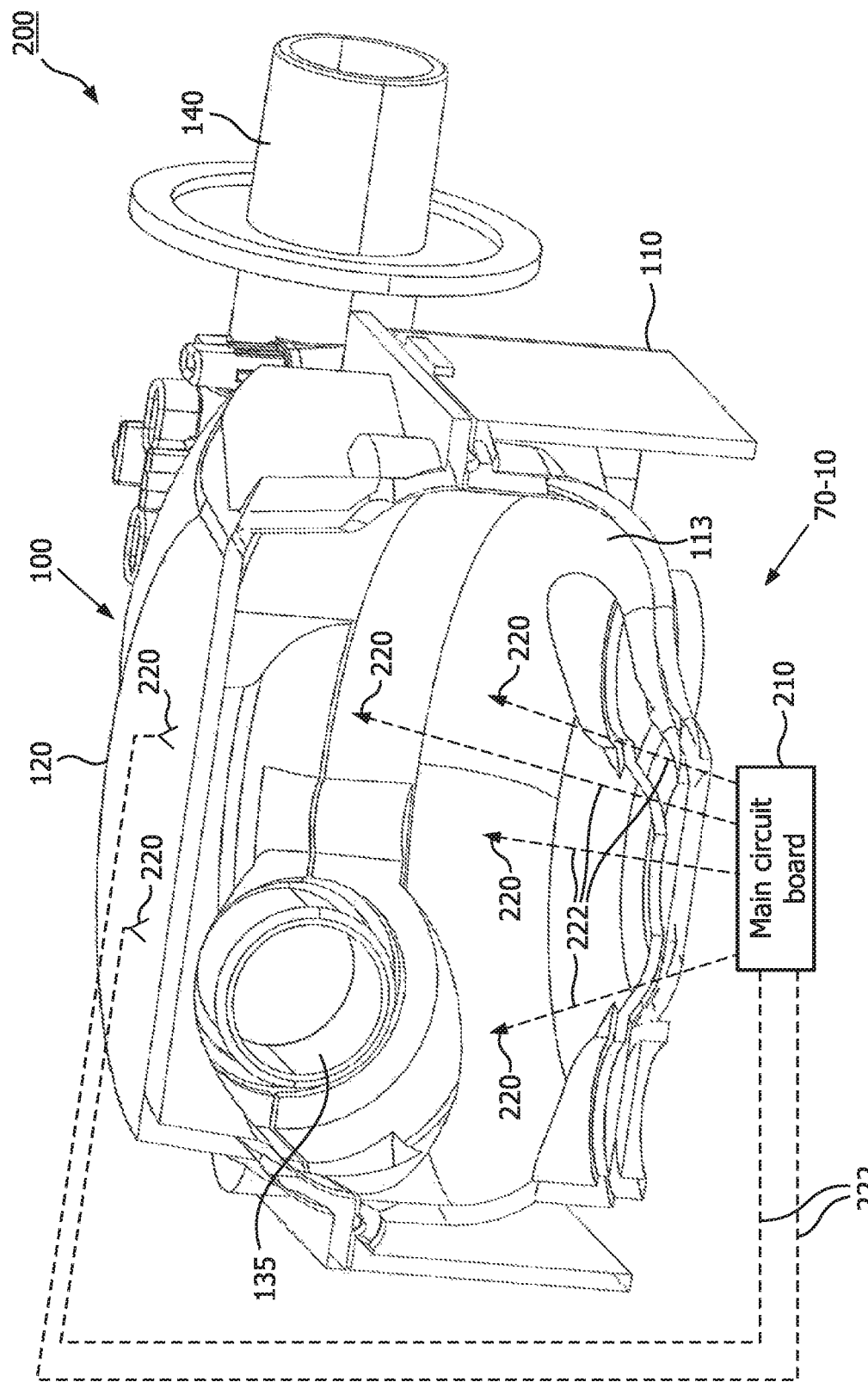
FIG. 10 is a cross-sectional view of a portion of the blower assembly of FIG. 2 in accordance with an embodiment of the disclosed concept.

FIG. 10 is a cross-sectional view of a first implementation, labeled 200, of blower assembly 100 having an embodiment of ultraviolet light system 70, labeled 70-10, integrated therewith. For ease of illustration, implementation 200 is shown without impeller assembly 130 provided therein. It will be appreciated, however, that in actual use, impeller assembly 130 will be included. In the present embodiment, ultraviolet light system 70-10 includes a main circuit board 210, a number of $UV_c$ light emitting diodes (LEDs) 220 (shown schematically in FIG. 10) that are embedded within various locations of blower assembly 100, and a number of wires 222 that run from and couple main circuit board 210 to LEDs 220. In the illustrated embodiment, LEDs 220 are embedded within main body portion 113 of lower housing 110 and within upper housing 120 such that they will shine $UV_c$ ultraviolet light on the surfaces of those components over which breathing gas is caused to flow as described herein. In addition, in further embodiments, LEDs 220 may also be embedded within other portions of the "inlet manifold", such as in directing wall 112, within portions of impeller assembly 130, such as in upper housing 131 and/or lower housing 132, and within portions of the "outlet manifold", such as partial conduits 116,121 and/or outlet conduit 140. In operation, main circuit board 210 is structured to energize LEDs 220, which in turn emit $UV_c$ ultraviolet light and thereby sanitize the nearby surfaces within blower assembly 100.

Figure 11:
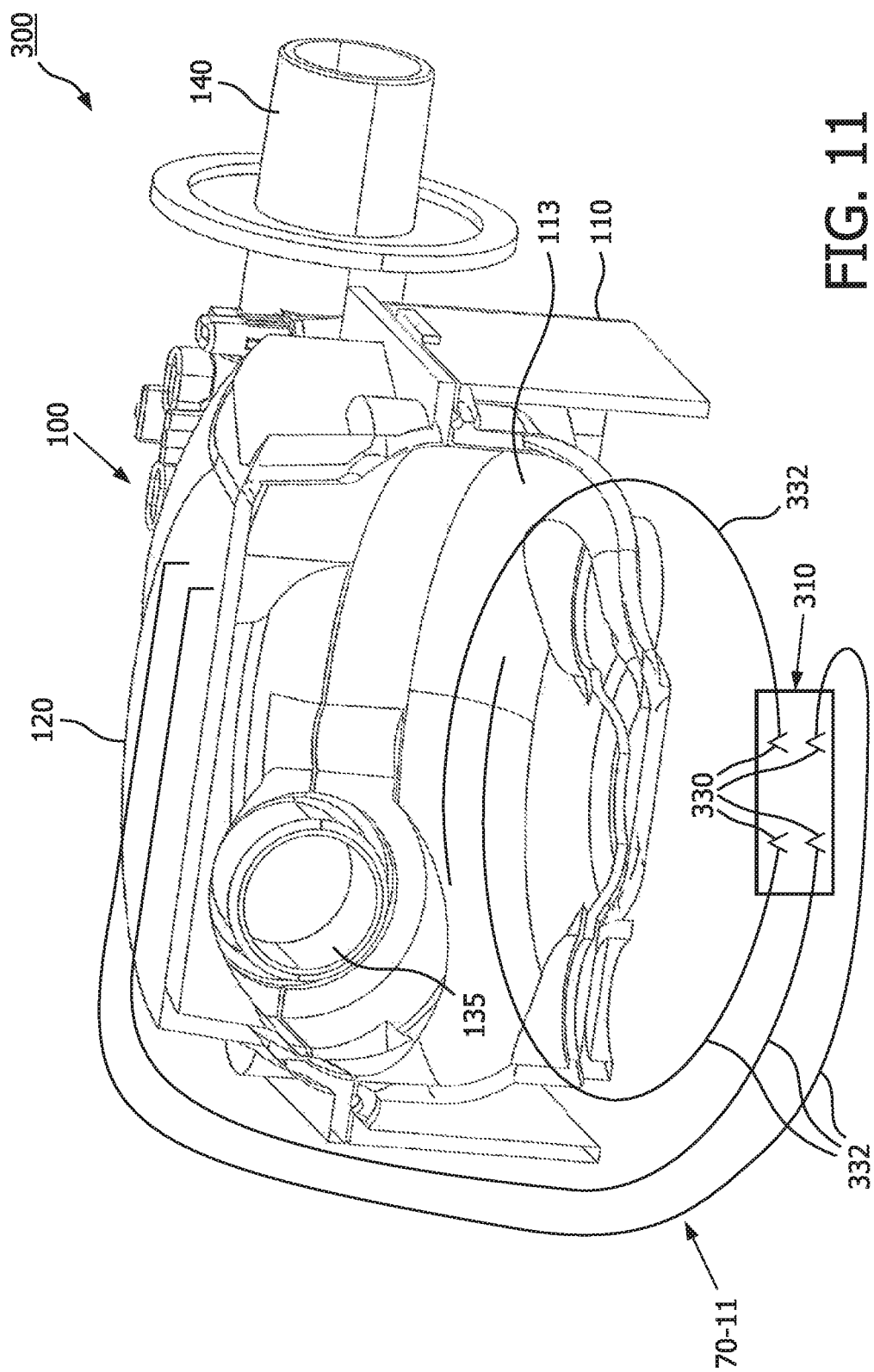
FIG. 11 is a cross-sectional view of a portion of the blower assembly of FIG. 2 in accordance with another embodiment of the disclosed concept.

FIG. 11 shows a cross-sectional view of a second implementation, labeled 300, of blower assembly 100 having an alternative embodiment of ultraviolet light system 70 (labeled 70-11) integrated therewith. For ease of illustration, implementation 300 is shown without impeller assembly 130 provided therein. In this embodiment, ultraviolet light system 70-11 includes a main circuit board 310, a number of $UV_c$ LEDs 330 located on main circuit board 310, and a number of light pipes 332 (e.g., without limitation, optical fibers, transparent plastic rods, or similar light transmitting members) that are coupled to LEDs 330 and embedded within and run along various portions of blower assembly 100. In particular, as shown in FIG. 11, each light pipe 332 has a first, light receiving end that is coupled to one of the LEDs 330, and a second, light emitting end that is positioned at a selected location within blower assembly 100. . In the present embodiment, light pipes 332 may be run to any of the locations described in connection with FIG. 10 at LEDs 220 may be mounted. In operation, LEDs 330 generate and pass $UV_c$ ultraviolet light through light pipes 332, which emit the light to and thereby sanitize the various surfaces within blower assembly 100.

Figure 12:
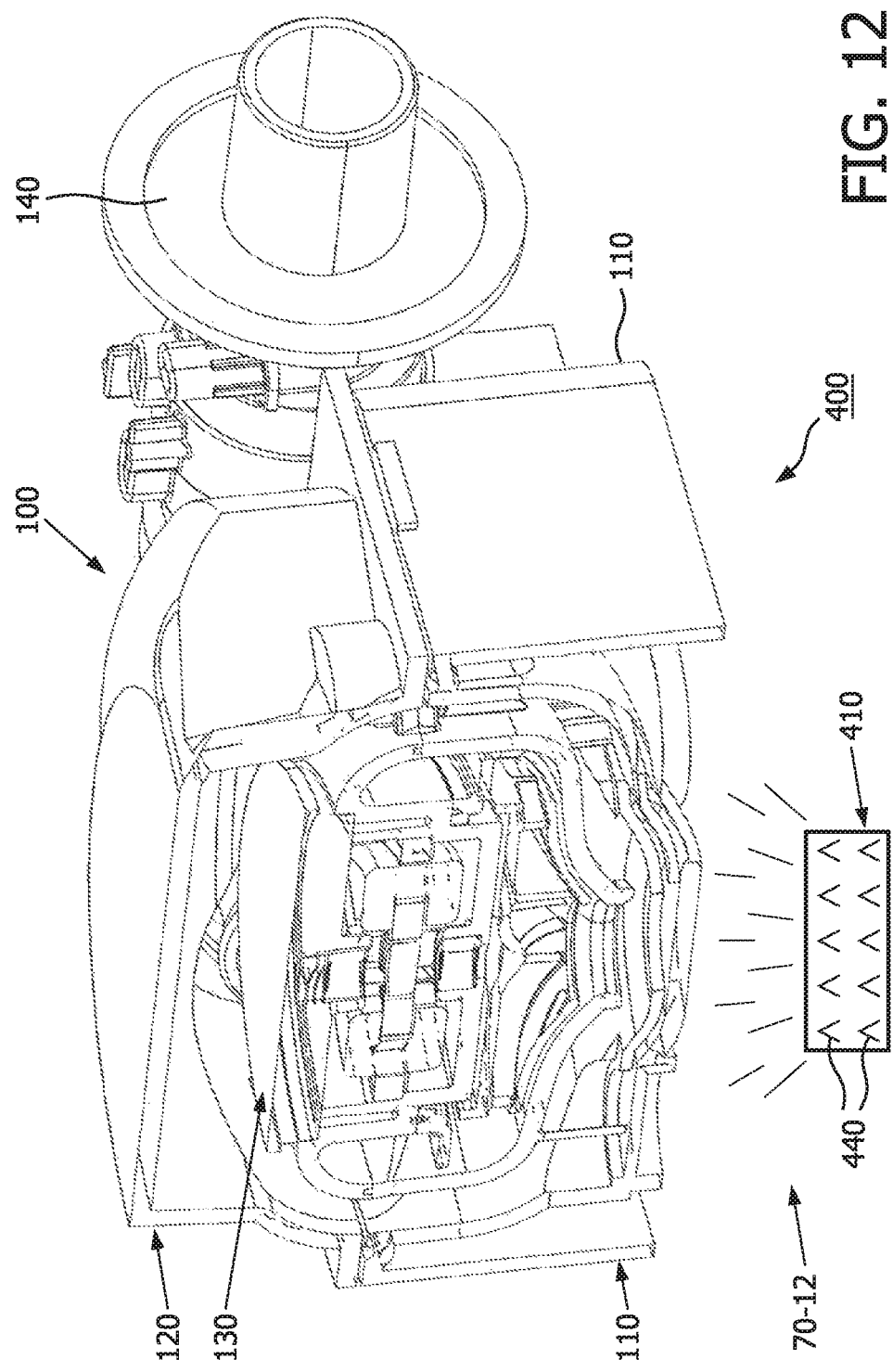
FIG. 12 is a cross-sectional view of the blower assembly of FIG. 2 in accordance with another embodiment of the disclosed concept.

FIG. 12 shows a cross-sectional view of a third implementation, labeled 400, of blower assembly 100 having another alternative embodiment of ultraviolet light system 70 (labeled 70-12) integrated therewith. In this embodiment, ultraviolet light system 70-12 includes a main circuit board 410 and a number of $UV_c$ LEDs 440 located on main circuit board 410 that emit $UV_c$ ultraviolet light when energized. In accordance with this embodiment, a number of components of blower assembly 100 (e.g., without limitation, one or more components of the "inlet manifold", "outlet manifold", and/or impeller assembly 130) are made of a material that is transparent to $UV_c$ ultraviolet light. As used herein, the term "transparent" shall mean that light is permitted to pass through the material and shall include, without limitation, situations where the light is diffused (translucency) and not diffused. For example, the transparent material may be an amorphous polymer such as but not limited to polycarbonate, acrylonitrile butadiene styrene (ABS), or polystyrene.

Thus, $UV_c$ ultraviolet light emitted from LEDs 440 passes through selected components of blower assembly 100 and as a result sanitizes the internal surfaces of those components.

Figure 13:
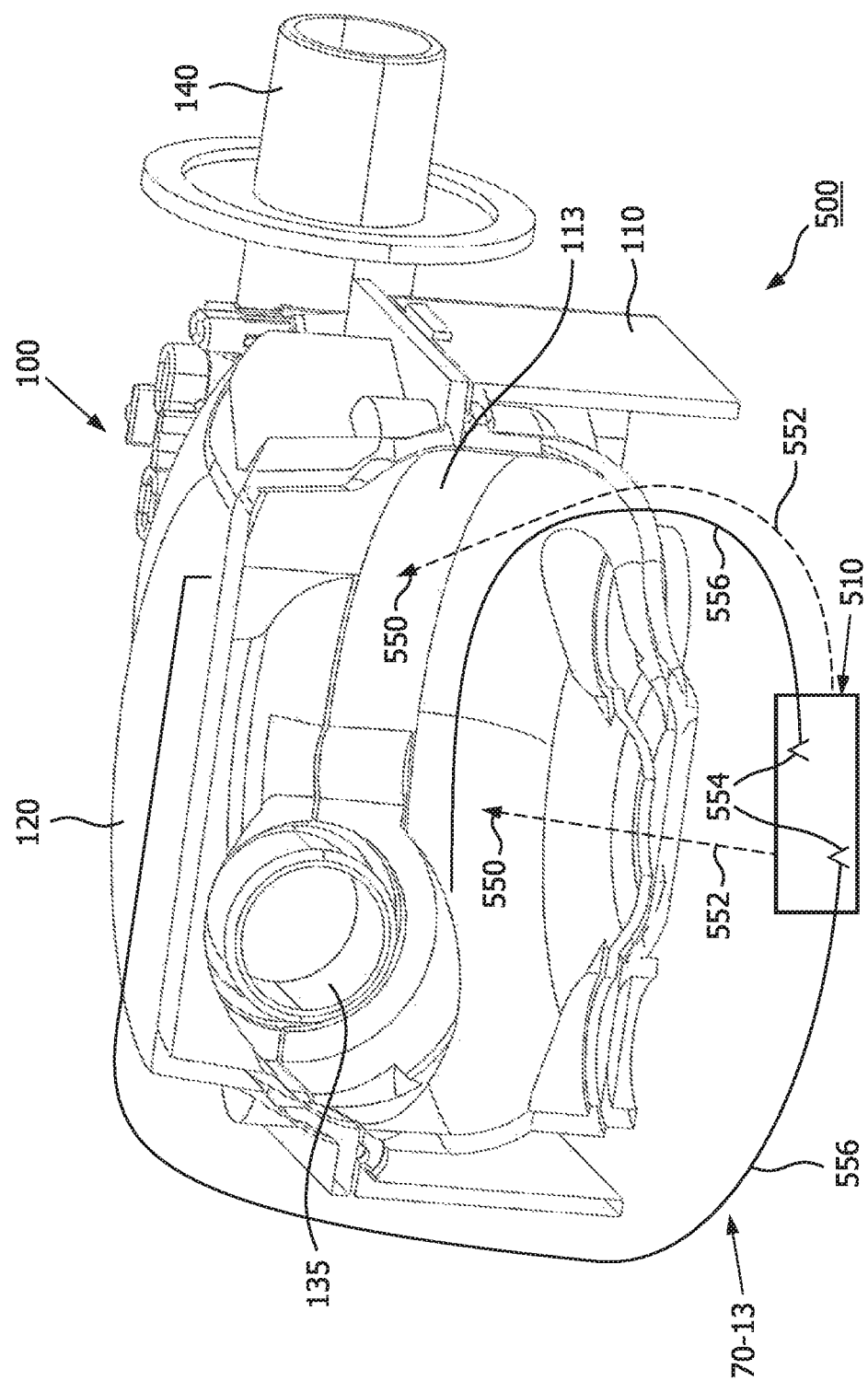
FIG. 13 is a cross-sectional view of a portion of the blower assembly of FIG. 2 in accordance with another embodiment of the disclosed concept.

FIG. 13 shows a cross-sectional view of a fourth implementation, labeled 500, of blower assembly 100 having yet another alternative embodiment of ultraviolet light system 70 (labeled 70-13) integrated therewith. For ease of illustration, impeller assembly 130 has once again been omitted. In this embodiment, ultraviolet light system 70-13 includes a main circuit board 510, a number of $UV_c$ LEDs 550 embedded within certain components of blower assembly 100 that emit $UV_c$ ultraviolet light when energized, and a number of wires 552 that couple LEDs 550 to main circuit board 510. Additionally, ultraviolet light system 70-13 includes another number of $UV_c$ LEDs 554 provided on main circuit board 510 that emit $UV_c$ ultraviolet light when energized and a number of light pipes 556 that run from main circuit board 510 and are embedded within certain components of blower assembly 100. In operation, LEDs 550 and light pipes 556 emit $UV_c$ ultraviolet light and combine to sanitize selected surfaces within blower assembly 100. Implementation 500 is thus a combination of implementation 200 of FIG. 10 and implementation 300 of FIG. 11. Additionally, although blower assembly 500 has been described in association with two embedded LEDs 550 and two light pipes 556, it is within the scope of the disclosed concept to have any number, configuration, and/or combination of LEDs and light pipes.

Figure 14:
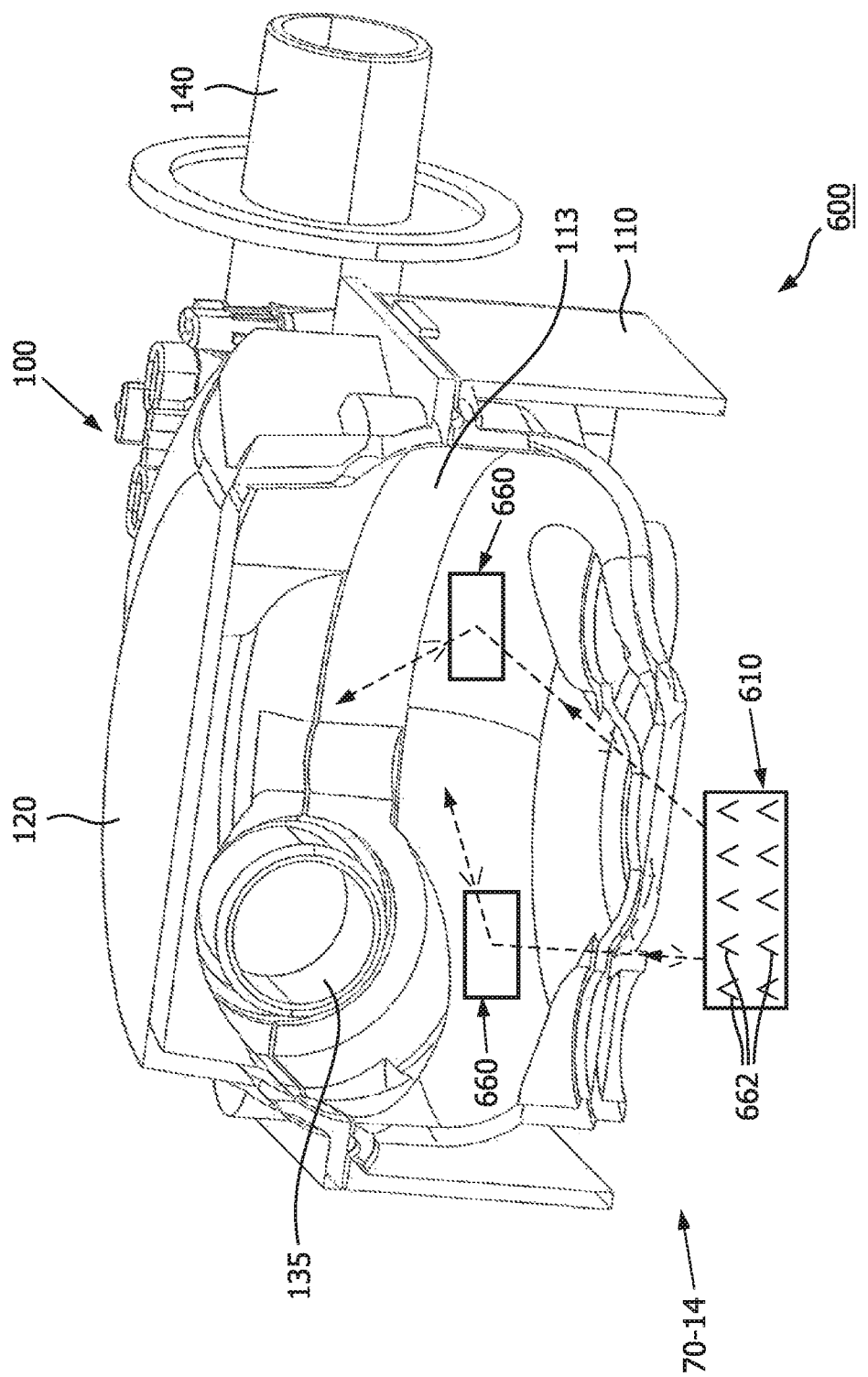
FIG. 14 is a cross-sectional view of a portion of the blower assembly of FIG. 2 in accordance with another embodiment of the disclosed concept.

FIG. 14 shows a cross-sectional view of a fifth implementation, labeled 600, of blower assembly 100 having still another alternative embodiment of ultraviolet light system 70 (labeled 70-14) integrated therewith. For ease of illustration, impeller assembly 130 has once again been omitted. In this embodiment, ultraviolet light system 70-14 includes a main circuit board 610, a number of light reflective surfaces 660 located within blower assembly 100, and a number of $UV_c$ LEDs 662 provided on main circuit board 610 that emit $UV_c$ ultraviolet light when energized. For example and without limitation, the light reflective surfaces may be an inserted metallic component or foil, or a metallic coating that is plated, sprayed or applied to the base material. In accordance with this embodiment, a number of components of blower assembly 100 (e.g., without limitation, one or more components of the "inlet manifold", "outlet manifold", and/or impeller assembly 130) are made of a material that is transparent to $UV_c$ ultraviolet light. In implementation 600 of blower assembly 100, $UV_c$ ultraviolet light emitted from LEDs 662 is structured to pass through selected components, contact reflective surfaces 660, and as seen, reflect in different directions, advantageously allowing for more surfaces to be reached and thereby sanitized by the $UV_c$ ultraviolet light. Although LEDs 662 are shown as employed on main circuit board 610, it is within the scope of the disclosed concept to have LEDs and/or light pipes embedded within blower assembly 100 (as described elsewhere herein), to emit light which reflects off of reflective surfaces 660 and thereby reaches and sanitizes more surfaces. Such an implementation is described below in connection with FIG. 15.

Figure 15:
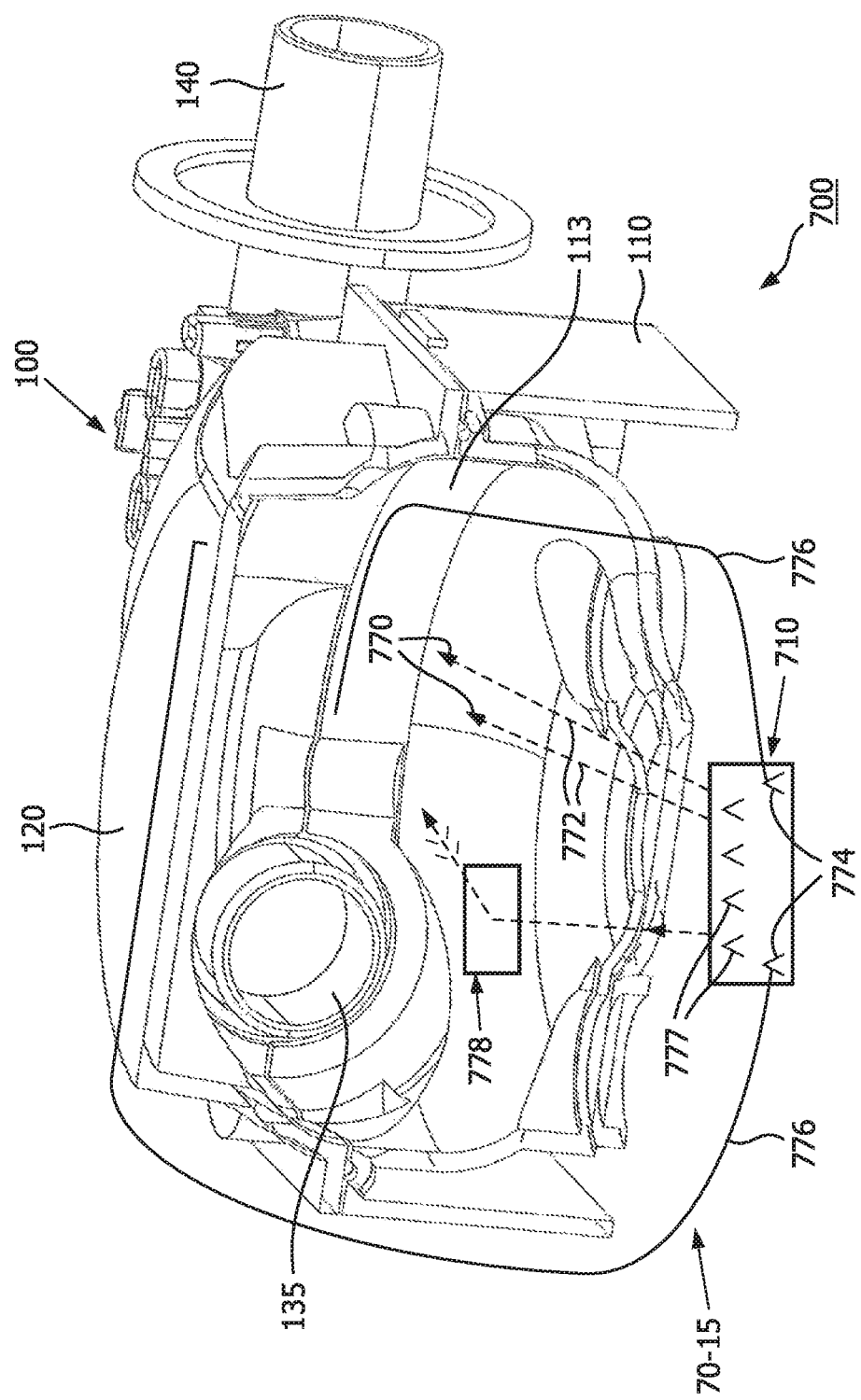
FIG. 15 is a cross-sectional view of a portion of the blower assembly of FIG. 2 in accordance with another embodiment of the disclosed concept.

FIG. 15 shows a cross-sectional view of a sixth implementation, labeled 700, of blower assembly 100 having still another alternative embodiment of ultraviolet light system 70 (labeled 70-15) integrated therewith. For ease of illustration, impeller assembly 130 has once again been omitted. In this embodiment, ultraviolet light system 70-15 includes a main circuit board 710, a number of $UV_c$ LEDs 770 that are embedded within various locations of blower assembly 100, and a number of wires 772 that couple LEDs 770 to main circuit board 710. Light system 70-15 also includes another number of $UV_c$ LEDs 774 located on main circuit board 710, a number of light pipes 776 that are coupled to LEDs 774 at one end thereof and that are embedded within blower assembly 100 as described elsewhere herein. Finally, light system 70-15 includes another number of $UV_c$ LEDs 777 that are located on main circuit board 710 and a reflective surface 778 provided on the internal surface of lower housing 110. In implementation 700 of blower assembly 100, a number of components of blower assembly 100 (e.g., without limitation, one or more components of the "inlet manifold", "outlet manifold", and/or impeller assembly 130) are made of a material that is transparent to $UV_c$ ultraviolet light. In this manner, light emitted from LEDs 777 on main circuit board 710 is structured to pass through selected components and contact reflective surface 778, thereby being able to reach more surfaces within blower assembly 100. Additionally, light emitted from LEDs 770 and/or light pipes 776 is likewise structured to reflect off of reflective surface 778 to reach and sanitize more surfaces within blower assembly 100. In operation, LEDs 770,774, 777, light pipes 776, and reflective surface 778 combine to allow $UV_c$ ultraviolet light to contact and thereby sanitize the various surfaces within blower assembly 100. Implementation 700 is thus a combination of implementations 200, 300, 400, and 600 described herein.

Additionally, it is within the scope of the disclosed concept to have any number, configuration and/or combination of $UV_c$ light sources, including but not limited to LEDs, light pipes, reflective surfaces, and/or transparent surfaces to allow for optimal sanitation within blower assembly 100. It is also within the scope of the disclosed concept to employ alternative $UV_c$ light sources not mentioned herein, such as, for example and without limitation, $UV_c$ light bulbs.

Thus, in accordance with the disclosed concept, the gas flow path (e.g., without limitation, "inlet manifold", impeller assembly 130, and "outlet manifold") within blower assembly 100 can be quickly and safely sanitized by an ultraviolet light system that emits sanitizing $UV_c$ light (e.g., without limitation, ultraviolet light systems 70-10,70-11,70-12,70-13,70-14,70-15).

Furthermore, ultraviolet light systems 70-10, 70-11, 70-12, 70-13, 70-14, and 70-15 as described herein may be energized and thereby caused to emit sanitizing light according to any of a number of suitable schemes or mechanisms. For example, and without limitation, ultraviolet light systems 70-10, 70-11, 70-12, 70-13, 70-14, and 70-15 may be structured to be energized manually (e.g., by a button) or automatically based on any of a number of conditions, such as expiration of a set timer, after a certain number of hours of use the pressure support system 50 is used, or whenever the pressure support system 50 is in use or is not in use.

The invention has been described in detail for the purpose of illustration based on what is currently considered to be the most practical exemplary embodiments. However, it is to be understood that such detail is solely for that purpose and that the invention is not limited to the disclosed embodiments, but, on the contrary, is intended to cover modifications and equivalent arrangements that are within the spirit and scope of the appended claims. For example and without limitation, the present invention is not limited to PAP therapy systems such as pressure support system 50, but rather ultraviolet light system 70 in the various embodiments described herein may be used with any type of gas delivery system used to deliver a flow of breathing gas to a patient, such as, without limitation, ventilators, oxygen delivery systems, or other respiratory devices.

What is claimed is:

1. A method of sanitizing a gas flow path within a gas delivery system including a blower assembly structured to generate a flow of breathing gas for delivery along the gas flow path, the blower assembly including an inlet manifold, an impeller assembly structured to adjust a pressure and/or flow rate of the flow of breathing gas, and an outlet manifold structured to be coupled to a patient circuit, the method comprising the steps of:

providing a light system as part of the gas delivery system;

generating sanitizing light from the light system; and delivering the sanitizing light to one or more internal surfaces of at least one of the inlet manifold, the impeller assembly, and the outlet manifold for sanitizing the one or more internal surfaces, wherein the sanitizing light is $UV_c$ ultraviolet light, and wherein the light system is an ultraviolet light system structured to generate the $UV_c$ ultraviolet light, further wherein the light system includes a circuit board, a number of $UV_c$ LEDs located on the circuit board for generating the $UV_c$ ultraviolet light, and a number of elongated light pipes, wherein each of the elongated light pipes is coupled to a corresponding one of the $UV_c$ LEDs, and wherein the $UV_c$ LEDs are structured to generate the $UV_c$ ultraviolet light and pass the $UV_c$ ultraviolet light through the elongated light pipes to deliver the $UV_c$ ultraviolet light to the one or more internal surfaces of at least one of the inlet manifold, the impeller assembly, and the outlet manifold.

2. The method of claim 1, wherein the elongated light pipes comprise at least one selected from the group consisting of optical fibers and transparent plastic rods.

3. The method of claim 1, wherein the light system further includes a number of $UV_c$ LEDs embedded within the blower assembly for generating the sanitizing light.

4. The method of claim 1, wherein at least one of the inlet manifold, the impeller assembly, and the outlet manifold is made of a material that is transparent to $UV_c$ ultraviolet light, and wherein the delivering includes passing the sanitizing light through the at least one of the inlet manifold, the impeller assembly, and the outlet manifold made of the material that is transparent to $UV_c$ ultraviolet light.

5. The method of claim 1, wherein the light system further includes a number of reflective surfaces disposed on a portion of at least one of the inlet manifold, the impeller assembly and the outlet manifold, the reflective surfaces being structured to reflect $UV_c$ ultraviolet light, and wherein the delivering includes reflecting the sanitizing light off of the reflective surfaces.

6. The method of claim 1, wherein the light system generates the $UV_c$ ultraviolet light in a range of 100 to 400 nanometers.

7. The method of claim 6, wherein the light system further generates the $UV_c$ ultraviolet light in a range of 200 to 280 nanometers.

8. A method of sanitizing a gas flow path within a gas delivery system including a blower assembly structured to generate a flow of breathing gas for delivery along the gas flow path, the blower assembly including an inlet manifold, an impeller assembly structured to adjust a pressure and/or flow rate of the flow of breathing gas, and an outlet manifold structured to be coupled to a patient circuit, the method comprising the steps of:

providing a light system as part of the gas delivery system;

generating sanitizing light from the light system; and delivering the sanitizing light to one or more internal surfaces of at least one of the inlet manifold, the impeller assembly, and the outlet manifold for sanitizing the one or more internal surfaces, wherein the sanitizing light is $UV_c$ ultraviolet light, and wherein the light system is an ultraviolet light system structured to generate the $UV_c$ ultraviolet light, further wherein the light system includes a circuit board and a number of $UV_c$ LEDs located on the circuit board for generating the $UV_c$ ultraviolet light, wherein at least one of the inlet manifold, the impeller assembly, and the outlet manifold is made of a material that is transparent to $UV_c$ ultraviolet light, and wherein the delivering includes passing the sanitizing light through the at least one of the inlet manifold, the impeller assembly, and the outlet manifold made of the material that is transparent to $UV_c$ ultraviolet light.

9. The method of claim 8, wherein the light system further includes a number of $UV_c$ LEDs embedded within the blower assembly for also generating the sanitizing light.

10. The method of claim 8, wherein the light system further includes a number of light transmitting members extending through one or more portions of the blower assembly, wherein each of the light transmitting members is coupled to a corresponding one of the $UV_c$ LEDs.

11. The method of claim 8, wherein the light system includes a number of elongated light pipes, wherein each of the elongated light pipes is coupled to a corresponding one of the $UV_c$ LEDs, and wherein the $UV_c$ LEDs are structured to generate the $UV_c$ ultraviolet light and pass the $UV_c$ ultraviolet light through the elongated light pipes to deliver the $UV_c$ ultraviolet light to the one or more internal surfaces of at least one of the inlet manifold, the impeller assembly, and the outlet manifold.

12. The method of claim 8, wherein the light system further includes a number of reflective surfaces disposed on a portion of at least one of the inlet manifold, the impeller assembly and the outlet manifold, the reflective surfaces being structured to reflect $UV_c$ ultraviolet light, and wherein the delivering includes reflecting the sanitizing light off of the reflective surfaces.

13. The method of claim 8, wherein the light system generates the $UV_c$ ultraviolet light in a range of 100 to 400 nanometers.

14. The method of claim 13, wherein the light system further generates the $UV_c$ ultraviolet light in a range of 200 to 280 nanometers.

15. A method of sanitizing a gas flow path within a gas delivery system including a blower assembly structured to generate a flow of breathing gas for delivery along the gas flow path, the blower assembly including an inlet manifold, an impeller assembly structured to adjust a pressure and/or flow rate of the flow of breathing gas, and an outlet manifold structured to be coupled to a patient circuit, the method comprising the steps of:

providing a light system as part of the gas delivery system;

generating sanitizing light from the light system; and delivering the sanitizing light to one or more internal surfaces of at least one of the inlet manifold, the impeller assembly, and the outlet manifold for sanitizing the one or more internal surfaces, wherein the sanitizing light is $UV_c$ ultraviolet light, and wherein the light system is an ultraviolet light system structured to generate the $UV_c$ ultraviolet light, further wherein the light system includes (i) a first number of $UV_c$ LEDs embedded within a portion of at least one of the inlet manifold, the impeller assembly, and the outlet manifold of the blower assembly, and (ii) a second number of $UV_c$ LEDs disposed on a circuit board and a number of light transmitting members extending through one or more portions of the blower assembly, wherein each of the light transmitting members is coupled to a corresponding one of the second number of $UV_c$ LEDs.

16. The method of claim 15, wherein at least one of the inlet manifold, the impeller assembly, and the outlet manifold is made of a material that is transparent to $UV_c$ ultraviolet light, and wherein the delivering includes passing the sanitizing light through the at least one of the inlet manifold, the impeller assembly, and the outlet manifold made of the material that is transparent to $UV_c$ ultraviolet light.

17. The method of claim 15, wherein the light system further includes a number of reflective surfaces disposed on a portion of at least one of the inlet manifold, the impeller assembly and the outlet manifold, the reflective surfaces being structured to reflect $UV_c$ ultraviolet light, and wherein the delivering includes reflecting the sanitizing light off of the reflective surfaces.

18. The method of claim 15, wherein the light transmitting members comprise elongated light pipes, wherein each of the elongated light pipes is coupled to a corresponding one of the second number of the $UV_c$ LEDs that are structured to generate the $UV_c$ ultraviolet light and pass the $UV_c$ ultraviolet light through the elongated light pipes to deliver the $UV_c$ ultraviolet light to the one or more internal surfaces of at least one of the inlet manifold, the impeller assembly, and the outlet manifold.

19. The method of claim 15, wherein the light system generates the $UV_c$ ultraviolet light in a range of 100 to 400 nanometers.

20. The method of claim 19, wherein the light system further generates the $UV_c$ ultraviolet light in a range of 200 to 280 nanometers.

* * * * *